United States Patent [19]

Dias et al.

[11] Patent Number: 5,509,417
[45] Date of Patent: Apr. 23, 1996

[54] METHOD AND APPARATUS FOR PHASED ARRAY COUPLING ULTRASONIC ENERGY INTO AN ACOUSTIC WAVEGUIDE WIRE

[75] Inventors: Fleming Dias, Palo Alto; Hewlett E. Melton, Jr., Sunnyvale, both of Calif.

[73] Assignee: Hewlett Packard Company, Palo Alto, Calif.

[21] Appl. No.: 358,279

[22] Filed: Dec. 19, 1994

[51] Int. Cl.⁶ .................................................. A61B 8/12
[52] U.S. Cl. ............................................... 128/662.06
[58] Field of Search ..................... 128/662.03, 662.06; 333/147, 149; 385/7, 123

[56] References Cited

U.S. PATENT DOCUMENTS

| | | | |
|---|---|---|---|
| 4,870,953 | 10/1989 | DonMichael et al. | 128/24 A |
| 5,284,148 | 2/1994 | Dias et al. | 128/662.06 |
| 5,304,115 | 4/1994 | Pflueger et al. | 604/22 |
| 5,400,788 | 3/1995 | Dias et al. | 128/662.06 |

*Primary Examiner*—George Manuel

[57] ABSTRACT

A method and apparatus for coupling ultrasonic energy into a clad or unclad waveguide include using phased array techniques to increase the area and intensity of radiation into the waveguide. An array of ultrasound transducers is positioned at the exterior of the waveguide and at dissimilar distances from the end of the waveguide. The transducers are individually fired by applying separate phase-shifted excitation signals. The phase shifting achieves a selected phase-differential relationship with respect to signals applied to adjacent transducers. The selected phase-differential relationship defines an angle of radiation into the waveguide. In the preferred embodiment, the apparatus is a medical device, such as an angioplasty device or ultrasound imaging device.

23 Claims, 5 Drawing Sheets

METHOD AND APPARATUS FOR PHASED ARRAY COUPLING ULTRASONIC ENERGY INTO AN ACOUSTIC WAVEGUIDE WIRE

TECHNICAL FIELD

The invention relates generally to apparatus and methods for generating and transmitting ultrasonic energy along an acoustic transmission line and more particularly to apparatus and methods for coupling ultrasonic energy into an invasive waveguide wire.

BACKGROUND ART

Within the medical field, ultrasonic systems are used for various imaging and/or treatment purposes. While many of the medical techniques may be non-invasive, i.e. only the ultrasound enters the body of interest, certain procedures require the introduction of a medical device into a person. Non-invasive ultrasonic imaging and treatment may be inadequate as a result of inaccessibility of tissue to an acoustic beam. A second concern relates to frequency. Higher ultrasonic frequencies are desirable, since short wavelengths enhance resolution. However, higher frequencies attenuate more rapidly, limiting the depth of penetration. At least to some degree, intracorporeal ultrasonic devices overcome these limitations.

One type of intracorporeal ultrasonic device is described in U.S. Pat. No. 4,870,953 to DonMicheal et al. The patent describes an apparatus and method for utilizing ultrasonic energy for the destruction of plaque or a blood clot in the blood-vessel. A hollow catheter is introduced into the blood vessel. An elongated, solid, flexible probe extends through the catheter. At a distal end of the probe is a blunt probe tip that is configured to minimize the likelihood that the probe tip will perforate the blood vessel. At the opposite, proximal end of the probe is a source of ultrasonic energy. Conventionally, the energy source abuts the end of the probe, so that the ultrasound is axially introduced into the probe for transmission along the length of the probe.

A similar device is described in U.S. Pat. No. 5,304,115 to Pflueger et al. The probe is referred to as an ultrasound transmission member and is formed of one or more superelastic metal alloys, such as a nickel-titanium alloy having a content of approximately 50.8 atomic percent nickel. Again, an ultrasonic energy source is coupled at a proximal end of the transmission member, while the distal end has a bulbous member. The bulbous distal end is caused to vibrate by operation of the energy source. The vibrations are designed to fracture arterial lesions and the like. Such angioplasty techniques have been successfully utilized.

Catheter-based imaging techniques are also known. Ultrasonic transducers may be located at the catheter end that is introduced into the body or at the catheter end that remains exterior to the body. Acoustic waves are directed at tissue of interest, whereafter reflected energy is detected. The reflections occur as a result of changes in acoustic impedance, so that time delays in receiving the reflections or phase changes of the reflections can be used to form images of organs or other tissue.

As previously noted, increases in frequency potentially enhance ultrasound image resolution. Higher frequencies are also preferred for angioplasty devices for pulverizing arterial lesions. However, conventionally ultrasound is at approximately 20 KHz for such applications, since ultrasound at higher frequency quickly attenuates when propagated through a transmission member such as the type described in DonMicheal et al. and Pflueger et al.

What is needed are an apparatus and a method for coupling ultrasonic energy to a longitudinal transmission line such that sufficient power is obtained for operation at high ultrasound frequencies.

SUMMARY OF THE INVENTION

An apparatus for generating and coupling ultrasonic energy to a flexible waveguide wire or the like includes an array of ultrasonic transducers, with the transducers being excited by excitation signals that are phase-shifted. That is, the excitation signal of an individual ultrasonic transducer has a phase-differential relationship with respect to signals applied to adjacent ultrasonic transducers. The preferred embodiment is one in which the transducers are directed and poled to transmit energy perpendicular to the axis of the waveguide wire. However, the transducers are operated such that deflection by means of phase shifting permits high-power transmission along the waveguide wire. Preferably, the radiation is deflected and focused, i.e., each transducer has a different angle of radiation in order to provide a focused ultrasound beam. Improved transmission efficiency is achieved by forming the waveguide wire to include a central core and an outer cladding. The outer cladding acts to confine acoustic energy to the central core during transmission from a proximal end to a distal end of the waveguide, in a similar manner to the use of an outer cladding to confine light energy within an optical fiber.

In the preferred embodiment, the ultrasonic transducers are annular members that are connected along a circumferential surface at a proximal end of the waveguide wire. The transducers are piezoelectric members that are poled in the radial direction. Using phased array principles, each segment of each annular transducer acts as a radiating body. For example, each transducer may be operatively associated with a different signal delay for defining the desired phase relationship. At the distal end of the waveguide wire, a bulbous member may be used to vibrate in response to acoustic energy generated by the transducers. When used in the medical field, the vibratory bulbous member acts to pulverize arterial lesions. However, the waveguide wire may also be a component of imaging equipment in which reflected ultrasonic energy is processed in a manner presently used for Doppler imaging. The phased array of transducers may be used to transmit the ultrasound beam, while a separate receiving transducer at the proximal end surface may be used to convert reflected ultrasonic energy into an electrical signal.

The annular transducers provide an advantage, since there is a greater transducer-to-wire contact area, increasing the power of transmitted energy. However, the exterior surface along the length of the proximal end of the waveguide wire may include one or more flat surfaces on which phased arrays are formed and operated. Increased transducer-to-waveguide wire contact area is still obtained, as compared to conventional devices in which the transducer is at the end surface perpendicular to the axis of the wire.

In another embodiment, separate phased transducer arrays are included. Each array may have a separate resonant frequency. For example, the thickness of the transducers of a first array may be different than the thicknesses of transducers of one or more other arrays. Since the thickness of a transducer bears an inverse relationship to the resonant frequency of the transducer, it becomes possible to select the frequency for transmission along the waveguide wire. Such a selection may be desirable for applications such as angioplasty, wherein different arterial lesions and the like react differently to various frequencies.

In yet another embodiment, annular transducers of a phased array are each separated into sections. If all of the sections of each transducer are activated simultaneously, the phased array will function in much the same manner as described above. However, if the transducer sections are excited in a spiraling order, the firing sequence will produce a spirally oriented beam, rather than a substantially rectilinear beam. The spirally oriented beam may be utilized to augment the cavitational efficiency of the bulbous member of an angioplasty device.

In another embodiment, coupling between the phased array and the waveguide wire is achieved by means of a liquid. The selection of the liquid depends upon the velocity of the ultrasonic energy of the transducers and the waveguide wire. As the ultrasonic energy passes from one medium to another, the relative velocities will determine the entry angle. Thus, different fluids will define different transmission paths.

An advantage of the invention is that the increased transducer-to-waveguide wire contact area increases the ultrasonic power through the waveguide wire. Consequently, higher frequencies may be used without unacceptable signal attenuation. Another advantage is that in embodiments in which the outer cladding is utilized to confine acoustic energy to propagation in the desired direction, less signal loss is experienced.

BEST MODE FOR CARRYING OUT THE INVENTION

Figure 1:
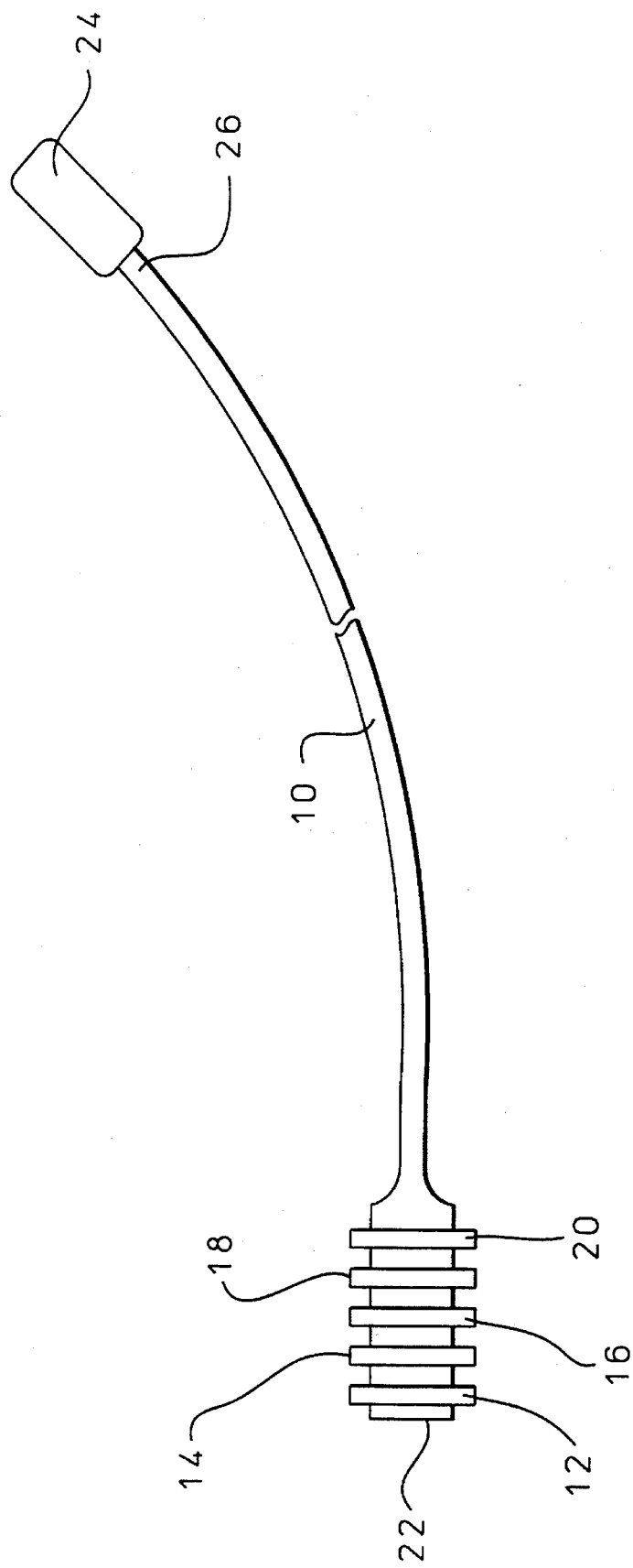
FIG. 1 is a perspective view of an ultrasound angioplasty apparatus having a phased array of transducers in accordance with the invention.

With reference to FIG. 1, an angioplasty apparatus includes a waveguide wire 10 having a phased array of ultrasonic transducers 12, 14, 16, 18 and 20 at a proximal end 22. A bulbous member 24 is secured at a distal end 26 of the waveguide wire. Conventionally, the waveguide wire is housed within a catheter that is dimensioned for insertion into a blood vessel of a person, through an incision made on the blood vessel for that purpose.

The bulbous member 24 is of the type known in the art. The bulbous member fits through a bore of the catheter. The member vibrates in response to ultrasonic energy transmitted from the ultrasonic transducers 12–20 via the waveguide wire 10. Conventionally, an angioplasty apparatus vibrates at approximately 20 KHz, since higher frequencies attenuate rapidly with passage through the apparatus. However, the phased array of transducers allows an increase in the input of power into the waveguide wire 10, so that higher frequencies may be employed.

Vibration of the bulbous member 24 may be used to dislodge arterial lesions from a blood vessel. Preferably, the catheter of the apparatus includes a passageway through which dislodged material may be suctioned. Operation of an angioplasty apparatus for treatment of a site of a blood vessel is known in the art.

The waveguide wire 10 may be formed in a manner known in the art. For example, U.S. Pat. No. 5,304,115 to Pflueger et al. describes an ultrasound transmission member that is formed of one or more superelastic metal alloys, such as a nickel-titanium alloy having a content of approximately 50.8 atomic percent nickel. However, in the preferred embodiment the waveguide wire includes an outer cladding surrounding a central core. The purpose of the cladding is to keep the acoustic energy within the waveguide wire. When the materials for the cladding and the central core are sufficiently different with respect to acoustic impedance, acoustic energy is confined within the waveguide assembly, since the acoustic energy reflects off the cladding and stays within the central core. Thus, the waveguide wire operates in the same manner as an optical fiber having an outer cladding. An acoustic waveguide having an outer cladding is described in U.S. Pat. No. 5,284,148 to Dias et al., which is assigned to the assignee of the present invention.

While the invention is primarily described and illustrated as being used with an angioplasty apparatus for arterial treatment, this is not critical. As an example of other uses, a phased array of transducers 12–20 may be used in an imaging application. Ultrasonic energy may be transmitted from a proximal end portion 22 to a distal end portion 26 of an imaging device, whereafter energy reflected by human tissue is converted to an electrical signal that enables the tissue to be imaged. Doppler imaging is another possible application.

Each of the transducers 12–20 is formed of a material for efficiently converting electrical energy to acoustical energy. An acceptable material is lead zirconium titanate (PZT). The difference between the inside diameter and the outside diameter of the annularly shaped transducers is a factor in determining the resonant frequency of the transducers. There is an inverse relationship between the resonant frequency and the distance between the inside diameter and the outside diameter.

Figure 2:
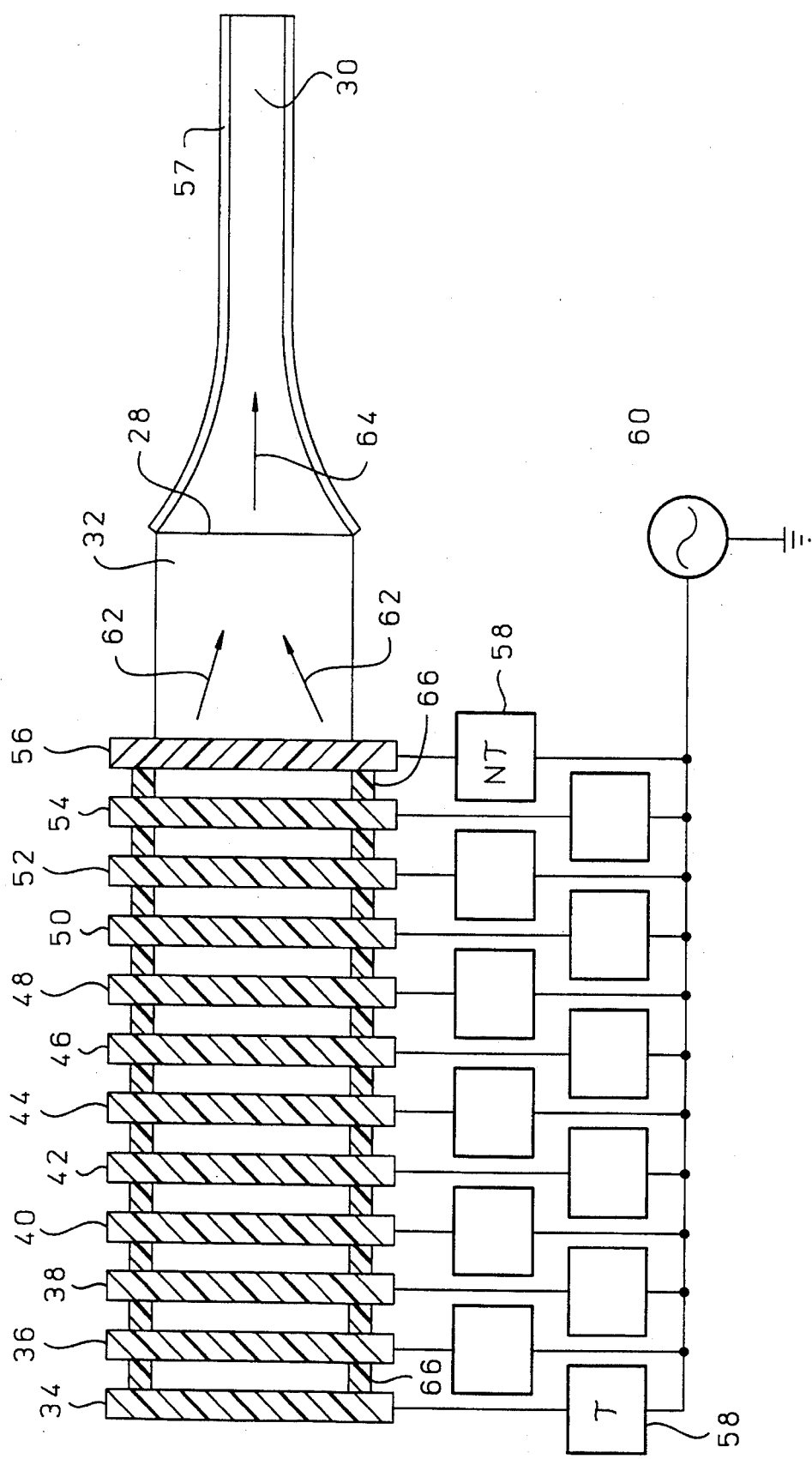
FIG. 2 is a side, partially sectional view of an apparatus for generating and transmitting ultrasonic energy along a waveguide wire in accordance with the invention.

Referring now to FIG. 2, a proximal end 28 of a waveguide wire 30 is abutted against a cylindrical member 32. However, in the preferred embodiment, the cylindrical member is a portion of the waveguide wire 30, so that energy is coupled directly from PZT transducers 34, 36, 38, 40, 42, 44, 46, 48, 50, 52, 54 and 56 to the wire. As previously noted, the waveguide wire may have a cladding 57 to confine the acoustic energy to the waveguide wire. Any number of materials may be used to form the outer cladding and the central core. For example, the central core may be formed of stainless steel, while the outer cladding may be a metal that is electroplated or sputtered around the core. Alternatively, the central core may be a liquid and the outer cladding may be a solid capillary tube.

Each of the PZT transducers 34–56 is operatively associated with a signal delay 58. The signal delays introduce phase shifts to excitation signals from a signal source 60. An ordered phase relationship is established in which an excitation signal to a particular transducer, e.g., transducer 46, has a selected phase differential with respect to signals to adjacent transducers 44 and 48. While not shown, each transducer has a first electrode at the inside diameter of the transducer and has a second electrode at the outside diameter of the transducer. The excitation signal of a transducer is applied across the transducer by means of the first and second electrodes. The PZT material is poled in a radial direction such that ultrasound radiation may be inwardly directed.

Operation of the array of transducers 34–56 is established by recognized principles relating to radiation from electromagnetic antennas and, more recently, ultrasound imaging by phased array devices. For example, it is known that an electromagnetic antenna consists of an array of radiating elements that are spaced apart by a distance (d) and are excited by electrical signals that differ in phase in a prescribed manner. In a linear array, the signals are of equal magnitudes, but have progressively increasing phase shifts. When the radiating elements are non-directional, the outgoing signal is determined to be $$E(\text{out}) = E_s[1 + \exp(j\psi) + \exp(2j\psi) + \exp(3j\psi) + \ldots \exp(j(n-1)\psi)] \quad (1)$$

where $E_s$ corresponds to the intensity of a single radiator and n is the number of radiators, and $$\psi = \beta d \cos\Theta + \alpha \quad (2)$$

where $\beta = 2\pi/\lambda$, and $\Theta$ is the direction of the main beam corresponding to the phase shift $\alpha$.

The first equation may be written as $$\begin{aligned} E(\text{out})/E_s &= [1 - \exp(jn\Psi)]/[1 - \exp(j\Psi)] \quad (3) \\ &= [\sin n\Psi/2]/[\sin \Psi/2] \end{aligned}$$

The maximum value of this expression is n, i.e., the number of radiating elements. This maximum value occurs at $\psi=0$.

If $\alpha=0$, i.e. there are no phase shifts between the radiating elements, then $\beta d \cos\Theta = 0$. In such case, $\Theta$ is 90 degrees. This may be referred to as a broad-fire operation of an array of radiating elements. In FIG. 2, broad-fire operation would be one in which each transducer 34–56 radiates ultrasonic energy in a perpendicular direction to the axis of the cylindrical member 32, i.e. the radiation is radially directed. However, a broad-fire operation is not desirable for the transducer of FIG. 2.

If a phase shift of $\alpha$ is introduced by the signal delays 58, then $\Theta$ is less than 90 degrees. Radiation then has a component of direction that is parallel to the axis of the cylindrical member 32. In FIG. 2, arrows 62 represent an ultrasound beam from the array of PZT transducers 34–56. Arrow 64 represents energy for transmission along the waveguide wire 30. As previously noted, the preferred embodiment is one in which the waveguide wire and the cylindrical member 32 are a single unit, so that beam reflection is less likely to occur at proximal end surface 28.

Between each of the transducers 34–56 is an annular acoustic absorber 66. The absorbers reduce the likelihood that "cross talk" will occur between adjacent transducers. Preferably, the end of the cylindrical member 32 opposite to the waveguide wire 30 also includes an acoustic absorber.

Figure 3:
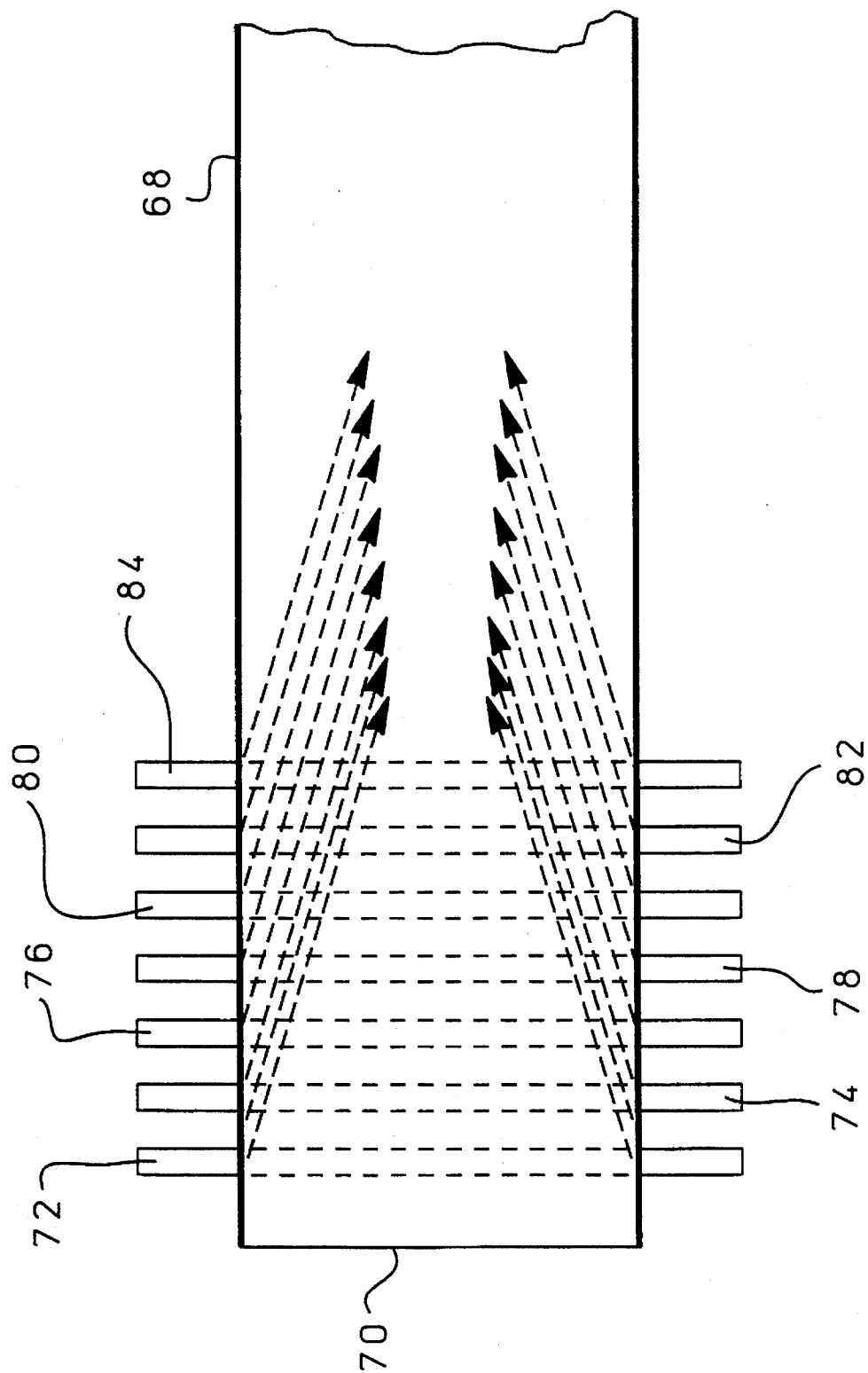
FIG. 3 is a side, operational view of a proximal end of a waveguide wire of FIG. 1.

Operation of the invention is best seen in FIG. 3. A cylindrical waveguide wire 68 has a cylindrical outer surface and a proximal end surface 70. An array of PZT transducers 72, 74, 76, 78, 80, 82 and 84 is connected to the circumferential surface of the waveguide wire. The annular transducers are individually excited. Separate phase-shifted excitation signals are applied to the transducers to form the array of ultrasound beams represented by the arrows in FIG. 3. The beams experience constructive and destructive interference to form a single high-power beam.

Each position along the inside diameter of each transducer 72–84 may be considered to be a radiating point. Corresponding positions of the transducers may therefore be considered to be an effective phased array. Consequently, the annular transducers act as a collection of simultaneously operated phased arrays.

In the embodiment of FIG. 3, the transducers radiate ultrasound beams which are all at the same angle to the axis of the waveguide wire 68. In the preferred embodiment, the phase relationship among the excitation signals to the transducers is selected to focus the ultrasonic energy. That is, the individual beams vary with respect to the angle to the axis such that the ultrasound radiation has a focal point. In this embodiment, the power of the resulting focused beam is further enhanced. However, beam focusing is not critical.

Figure 4:
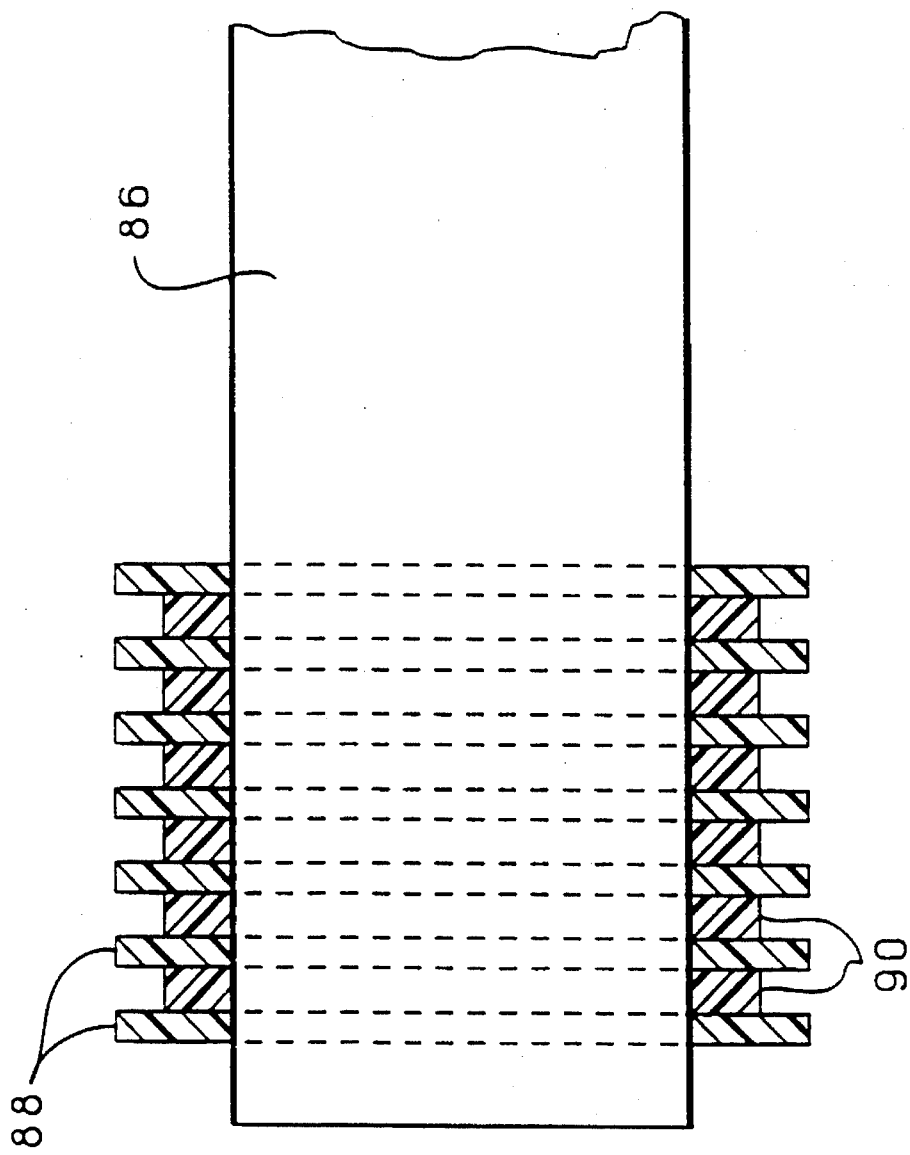
FIG. 4 is a second embodiment of the utilization of phased array principle to generate and transmit ultrasonic energy along a waveguide wire.

In the embodiment of FIG. 4, a cylindrical waveguide wire 86 includes a first array of ultrasonic transducers 88 and a second array of ultrasonic transducers 90. Typically, the two arrays will not be driven simultaneously. Instead, the transducers 90 will be excited when a high frequency transmission is required, while the transducers 88 will be driven when a somewhat lower frequency is desired. Since the thickness of a transducer is inversely related to the resonant frequency of the transducer, the embodiment of FIG. 4 permits a selection of frequencies. Different arterial lesions will react to various frequencies in a different manner. Thus, the selection of operating frequencies provides an advantage. Optionally, sequential pulses of different frequencies may be transmitted by alternating excitation of the two arrays.

Figure 5:
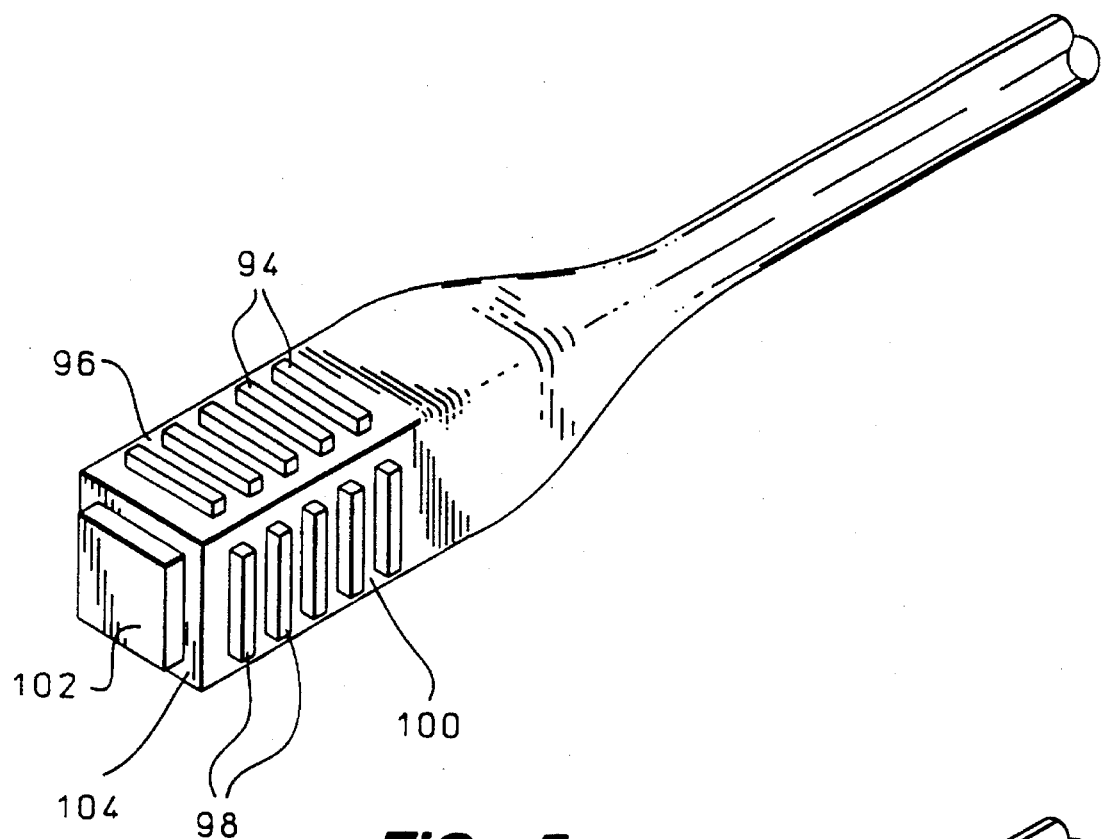
FIG. 5 is a perspective view of another embodiment of an apparatus for phased array coupling of ultrasonic energy into an acoustic waveguide wire.

In FIG. 5, a waveguide wire 92 has a circular cross section other than at an end portion associated with the distal end of the waveguide wire. The end portion includes a first phased array of transducers 94 on one planar surface 96 and a second phased array of transducers 98 on a second planar surface 100. The phased arrays are actuated using the radiation principles described above in order to transmit ultrasonic energy along the length of the waveguide wire 92. Optionally, the apparatus may have a receiver transducer 102 on a proximal end surface 104. The receiver transducer is positioned to detect reflected energy. That is, ultrasonic energy that is generated by the transducers 94 and 98 may be radiated at the distal end of the waveguide wire, whereafter energy that is reflected back to the distal end is retransmitted along the length of the waveguide wire for detection by the receiver transducer 102. In this manner, the waveguide wire may be used in an ultrasound imaging application. While the transducers 94 and 98 are shown as separate members, a single array of transducers having four linear segments may be used to achieve radiation from each of four sides of the proximal end portion.

Figure 6:
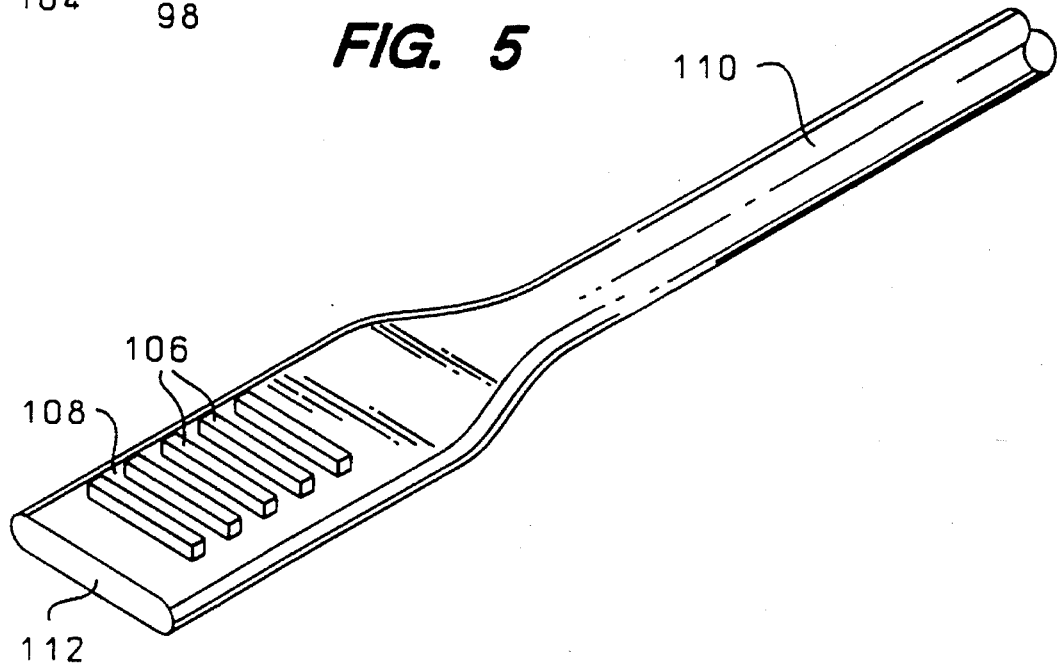
FIG. 6 is a perspective view of an embodiment of a single phased array for transmission of ultrasonic energy into an acoustic waveguide wire.

In the embodiment of FIG. 6, a single phased array of PZT transducers 106 is formed on a planar surface 108 of a proximal end portion of a waveguide wire 110. In the same manner as each of the previously described embodiments, the transducers are arranged such that there is an increase in distance from a proximal end surface 112.

Returning to FIG. 5, a spiraling ultrasound beam may be formed for transmission along the waveguide wire 92. In addition to the phased arrays on the planar surfaces 96 and 100, two additional phased arrays are located on the sides of the proximal end portion not seen in FIG. 5. If all four phased arrays are activated simultaneously, the resulting beam will follow a rectilinear path along the waveguide wire. On the other hand, firing the individual transducers 94 and 96 of the four phased arrays in a sequence that resembles spiraling activation will produce a spirally oriented beam. However, a spiraling beam may be more closely approximated if the proximal end portion of the waveguide wire is cylindrical and the transducers are increased in number and reduced in length. For example, an array of annular transducers may be segmented and positioned along the circumference of the cylindrical proximal end portion, and then fired in a spiraling fashion to generate the spiraling beam.

In each of the described and illustrated embodiments, an array of transducers is fixed to the outer surface of a waveguide wire. However, this is not critical. Surface acoustic wave (SAW) techniques may be utilized to radiate energy from a transducer array through a fluid and into a waveguide wire. Referring again to FIG. 6, the transducers 106 may be disposed along a planar surface that is spaced apart from a waveguide wire, not shown. The distance between the transducers and the waveguide wire may be filled with a fluid in which the longitudinal velocity of the fluid is less than the SAW velocity in the transducers. The transducers may be operated as interdigital transducers that are excited to radiate energy parallel to the surface 108 on which the transducers are positioned. The ultrasonic energy is then coupled to the waveguide wire by the utilization of leaky SAW and angle beam concepts. The surface acoustic waves leak into the fluid and become longitudinal waves. The longitudinal wave travels through the fluid at an angle given by Snell's law. When the longitudinal wave intersects the surface of the waveguide wire, Snell's law again determines an angle of entry into the wire. By selecting the various materials to achieve a desired angle of entry into the waveguide wire, a high-power ultrasound beam can be transmitted along the wire. Transmission power can be further enhanced by utilizing a cylindrical PZT shell, rather than an array of planar transducers. The waveguide wire should be concentric with the PZT shell, so that ultrasonic energy enters the waveguide wire about the entire circumference of the wire.

We claim:

1. An apparatus for generating and transmitting ultrasonic energy comprising:

a longitudinally extending transmission line having an input end, said input end having an axis;

an array of ultrasonic transducers in acoustic energy-transfer relationship with said transmission line, said ultrasonic transducers being at dissimilar distances from said input end; and excitation means connected to said ultrasonic transducers for applying a separate phase-shifted excitation signal to each ultrasonic transducer of said array, each said separate phase-shifted excitation signal applied to an ultrasonic transducer having a phase relationship with phase-shifted excitation signals applied to adjacent ultrasonic transducers of said array such that ultrasonic energy transmitted from said ultrasonic transducers is directed for conduction along said transmission line.

2. The apparatus of claim 1 wherein said excitation means includes a plurality of signal delays, each ultrasonic transducer being operatively associated with one of the signal delays for defining said phase relationship of a phase-shifted excitation signal to be applied to said each ultrasonic transducer.

3. The apparatus of claim 1 wherein said array of ultrasonic transducers is an array of coaxial annularly shaped piezoelectric transducers, each piezoelectric transducer being spaced apart from adjacent piezoelectric transducers.

4. The apparatus of claim 3 wherein said piezoelectric transducers are coaxial with said input end of said transmission line.

5. The apparatus of claim 3 wherein said transmission line has a cylindrical shape, said piezoelectric transducers being coaxial with said input end and being connected to the circumference of said cylindrically shaped transmission line.

6. The apparatus of claim 1 wherein said transmission line is a cladded-core waveguide having an outer cladding formed of first material and a central core formed of a second material.

7. The apparatus of claim 1 wherein said array of ultrasonic transducers is a linear array on a planar surface that is parallel to said axis of said input end.

8. The apparatus of claim 7 further comprising a second array of ultrasonic transducers on a second surface, said second array being in energy-transfer relationship with said transmission line.

9. The apparatus of claim 1 further comprising a bulbous member at an end of said transmission line opposite to said input end, said bulbous member being configured for insertion into a vessel of a human body.

10. The apparatus of claim 1 wherein said transmission line is a flexible wire.

11. The apparatus of claim 1 wherein said input end is cylindrical and has an outer circumference, each ultrasonic transducer being a segmented annulus having spaced apart segments arranged along said outer circumference, said excitation means being connected to each of said segments.

12. An apparatus for invasively transmitting ultrasonic energy into a body comprising:

a flexible waveguide wire having a proximal end and a distal end, said waveguide wire having an outer surface;

a phased array of ultrasonic transducers arranged along said outer surface near said proximal end; and a bulbous member at said distal end of said waveguide wire to vibrate in response to acoustic energy generated by said phased array.

13. The apparatus of claim 12 wherein each ultrasonic transducer is operatively associated with a signal delay means for establishing a selected phase relationship among adjacent ultrasonic transducers.

14. The apparatus of claim 12 further comprising a catheter, said waveguide wire extending axially through said catheter.

15. The apparatus of claim 12 wherein said waveguide wire has an outer cladding formed of a first material and a central core formed of a second material.

16. The apparatus of claim 12 wherein each ultrasonic transducer has an annular shape.

17. The apparatus of claim 12 further comprising a receiving ultrasonic transducer in energy-transfer relationship with said proximal end of said waveguide wire to receive reflected ultrasonic energy generated at said distal end.

18. A method of transmitting ultrasonic energy into a body comprising the steps of:

providing a waveguide wire having an input end having an axis and an outer surface;

attaching an array of ultrasonic transducers in energy-transfer relationship with said outer surface such that said ultrasonic transducers are at dissimilar distances relative to said input end; and individually exciting said ultrasonic transducers, including applying phase-shifted signals for which a signal applied to an ultrasonic transducer of said array has a selected phase-differential relationship with respect to signals applied to adjacent ultrasonic transducers, wherein ultrasonic signals generated by said ultrasonic transducers enter said waveguide wire via said outer surface.

19. The method of claim 18 wherein individually exciting said ultrasonic transducers includes delaying excitation signals in an ordered fashion.

20. The method of claim 18 wherein attaching said array is a step of connecting annular transducers to said outer surface of said waveguide wire.

21. The method of claim 18 further comprising attaching a bulbous member to an end of said waveguide wire opposite to said input end.

22. The method of claim 18 further comprising attaching a second array of ultrasonic transducers to said input end and individually exciting said ultrasonic transducers of said second array such that said exciting establishes a phase-differential order among said ultrasonic transducers.

23. The method of claim 18 further comprising forming a cladding on an exterior of said waveguide wire between said input end and an output end of said waveguide wire.

* * * * *